US005880210A

United States Patent [19]

Schulz, Jr. et al.

[11] Patent Number: 5,880,210

[45] Date of Patent: Mar. 9, 1999

[54] SILICONE FLUIDS AND SOLVENTS THICKENED WITH SILICONE ELASTOMERS

[75] Inventors: William James Schulz, Jr.; Shizhong Zhang, both of Midland, Mich.

[73] Assignee: Dow Corning Corporation, Midland, Mich.

[21] Appl. No.: 829,867

[22] Filed: Apr. 1, 1997

[51] Int. Cl.$^6$ .......... C08K 5/24

[52] U.S. Cl. .......... 524/731; 524/261; 524/379; 524/315; 524/356; 524/366; 524/354; 524/862; 528/15; 528/25; 528/502 F

[58] Field of Search .......... 528/15, 502 F, 528/25; 524/862, 261, 379, 315, 366, 356, 354, 731

[56] References Cited

U.S. PATENT DOCUMENTS

| | | | |
|---|---|---|---|
| 3,715,334 | 2/1973 | Karstedt | 260/46 |
| 3,814,730 | 6/1974 | Karstedt | 260/46 |
| 4,987,169 | 1/1991 | Kuwata | 524/267 |
| 5,493,041 | 2/1996 | Biggs | 556/453 |
| 5,654,362 | 8/1997 | Schulz, Jr. et al. | 524/862 |

*Primary Examiner*—Melvyn I. Marquis
*Assistant Examiner*—Caixia Lu-Rutt
*Attorney, Agent, or Firm*—James De Cesare

[57] ABSTRACT

Silicone gels are made by reacting an ≡Si—H containing polysiloxane with an alpha-olefin and an alpha, omega-diene. The reaction is conducted in the presence of a platinum catalyst and in the presence of a low molecular weight silicone oil. First, an ≡Si—H containing polysiloxane is grafted by long chain alkyl groups from the alpha-olefin onto the ≡Si—H containing polysiloxane, and then crosslinked with double bonds in the alpha, omega-diene, in the presence of the low molecular weight silicone oil. The formed silicone gel can then be crumbled into a silicone powder using mechanical force. When additional amounts of the low molecular weight silicone oil are added to the gel, and the silicone oil and the gel are subjected to shear force, a silicone paste can be formed.

24 Claims, No Drawings

SILICONE FLUIDS AND SOLVENTS THICKENED WITH SILICONE ELASTOMERS

CROSS-REFERENCE TO RELATED APPLICATIONS

This application is an improvement in subject matter described in our prior copending application U.S. Ser. No. 08/618,616, filed on Mar. 20, 1996, U.S. Pat. No. 5,654,362, entitled “Silicone Oils and Solvents Thickened by Silicone Elastomers”. The prior application is assigned to the same assignee as this application.

STATEMENT REGARDING FEDERALLY SPONSORED RESEARCH OR DEVELOPMENT

Not applicable.

REFERENCE TO A MICROFICHE APPENDIX

Not applicable.

BACKGROUND OF THE INVENTION

This invention is directed to thickened silicone oils in the form of silicone elastomers swollen into silicone gels, silicone pastes, or silicone powders.

Cross-links are junctions of polymer strands in a three-dimensional network. They may be viewed as long-chain branches which are so numerous that a continuous insoluble network or gel is formed.

Increasingly, platinum catalyzed hydrosilylation reactions are being used to form networks. They typically involve reactions between a low molecular weight polysiloxane containing several ≡Si—H groups, and a high molecular weight polysiloxane containing several ≡Si-vinyl groups, or vice versa.

Attractive features of this mechanism are that (i) no by-products are formed, (ii) cross-linking sites and hence network architecture can be narrowly defined, and (iii) hydrosilylation will proceed even at room temperature to form the networks. In the mechanism, crosslinking involves addition of ≡SiH across double bonds, i.e., ≡SiH+ $CH_2$═CH—R→≡Si$CH_2CH_2$—R.

We have utilized this mechanism, but by employing some unobvious and unique modifications of the mechanism, we have been able to formulate a new range of product forms having new and unique properties and ranges of application.

BRIEF SUMMARY OF THE INVENTION

Our invention relates to methods of thickening silicone oils or other solvents to gel-like consistency by reacting (A) a first ≡Si—H containing polysiloxane of the formula $R_3SiO(R'_2SiO)_a(R''HSiO)_bSiR_3$ and optionally a second ≡Si—H containing polysiloxane of the formula $HR_2SiO(R'_2SiO)_cSiR_2H$ or the formula $HR_2SiO(R'_2SiO)_a(R''HSiO)_bSiR_2H$ where R, R', and R"are alkyl groups with 1–6 carbon atoms; a is 0–250; b is 1–250; and c is 0–250;(B) an alpha-olefin of the formula $CH_2$═'"R"" where R'" is hydrogen or an alkyl group containing 1–40 carbon atoms, and R"" is an alkyl group containing 1–40 carbon atoms; and (C) an alpha, omega-diene of the formula $CH_2$═$CH(CH_2)_xCH$═$CH_2$ where x is 1–20. The reaction is conducted in the presence of a platinum catalyst, and in the presence of (D) a low molecular weight silicone oil or other solvent.

The low molecular weight silicone oil is preferably a volatile oil, although non-volatile oils can also be used. The reaction is carried out by first grafting long chain alkyl groups from the alpha-olefin onto the ≡Si—H containing polysiloxane, and then crosslinking and addition of ≡Si—H in the grafted ≡Si—H containing polysiloxane across double bonds in the alpha, omega-diene, until a gel is formed In a second embodiment, we crumble the silicone gel into a silicone powder using mechanical force.

In a third embodiment, we add additional low molecular weight silicone oil to the gel, and subject the oil and the gel to shear force, until a silicone paste is formed.

These and other objects of our invention will become apparent from a consideration of the following detailed description.

BRIEF DESCRIPTION OF THE SEVERAL VIEWS OF THE DRAWING

Not applicable.

DETAILED DESCRIPTION OF THE INVENTION

Silicone elastomers are prepared by a grafting and crosslinking reaction between (A) an ≡Si—H containing polysiloxane, (B) an alpha-olefin, (C) an alpha, omega-diene, in the presence of a platinum catalyst and (D) a low molecular weight linear or cyclic silicone oil. The elastomers can be swollen with the low molecular weight silicone oil under a shear force. Elastomers containing 65–98 weight percent of the low molecular weight silicone oil are stable and form uniform silicone pastes with a wide viscosity range.

The silicone pastes have excellent properties including clarity, thixotropy, shear thinning, and spread smoothly on the skin. They can be applied in cosmetic and medical products as the base oil. The silicone elastomers are capable of being crumbled to form a silicone powder. The silicone powder has the unique property of being easily rubbed-in on the skin, and silicone resins can be incorporated therein to improve the substantivity of formulations applied to the skin. These materials are ideal for use in solid cosmetics such as antiperspirants and deodorants.

The ≡Si—H containing polysiloxane (A) is represented by compounds of the formula $R_3SiO(R'_2SiO)_a(R''HSiO)_bSiR_3$ designated herein as type $A^1$ and compounds of the formula $HR_2SiO(R'_2SiO)_cSiR_2H$ or formula $HR_2SiO(R'_2SiO)_a(R''HSiO)_bSiR_2H$ designated herein as type $A^2$. In these formulas, R, R', and R", are alkyl groups with 1–6 carbon atoms; a is 0–250; b is 1–250; and c is 0–250. The molar ratio of compounds $A^2$:$A^1$ is 0–20, preferably 0–5. In our most preferred embodiment, compounds of types $A^1$ and $A^2$ are used in the reaction, however, it is possible to successfully conduct the reaction using only compounds of type $A^1$.

The alpha-olefin (B) is a compound of the formula $CH_2$═CR'"R"" where R'" is hydrogen or an alkyl group containing 1–40 carbon atoms, and R"" is an alkyl group containing 1–40 carbon atoms. Some representative examples of suitable alpha-olefins for use herein are propene, 1-butene, isobutylene (2-methylpropene), 1-pentene (C5), 2-methyl-1-butene, 3-methyl-1-butene, 1-hexene, 2-methyl-1-pentene, 3-methyl-1-pentene, 4-methyl-1-pentene, 1-heptene, 2-methyl-1-hexene, 1-octene, 2-methyl-1-heptene, 1-nonene, 1-decene (C10), 1-undecene, 1-dodecene, 1-tridecene, 1-tetradecene, 1-pentadecene (C15), 1-hexadecene, 1-octadecene, 1-nonadecene, 1-eicosene (C20), 1-heptacosene, and alpha-olefin fractions containing various amounts of C22–C30+ alpha-olefins sold under the trademark GULFTENE® 24–28 and GULFTENE® 30+ by the Chevron Chemical Company, Houston, Tex.

The alpha, omega-diene (C) is a compound of the formula $CH_2{=}CH(CH_2)_xCH{=}CH_2$ where x is 1–20. Some representative examples of suitable alpha, omega-dienes for use herein are 1,4-pentadiene; 1,5-hexadiene; 1,6-heptadiene; 1,7-octadiene; 1,8-nonadiene; 1,9-decadiene; 1,11-dodecadiene; 1,13-tetradecadiene; and 1,19-eicosadiene.

The grafting, addition, and crosslinking reactions require a catalyst to effect the reaction between the ≡SiH containing polysiloxane, the alpha-olefin, and the alpha, omega-diene. Suitable catalysts are Group VIII transition metals, i.e., the noble metals. Such noble metal catalysts are described in U.S. Pat. No. 3,923,705, incorporated herein by reference to show platinum catalysts. One preferred platinum catalyst is Karstedt's catalyst, which is described in Karstedt's U.S. Pat. Nos. 3,715,334 and 3,814,730, incorporated herein by reference. Karstedt's catalyst is a platinum divinyl tetramethyl disiloxane complex typically containing about one weight percent of platinum in a solvent such as toluene. Another preferred platinum catalyst is a reaction product of chloroplatinic acid and an organosilicon compound containing terminal aliphatic unsaturation. It is described in U.S. Pat. No. 3,419,593, incorporated herein by reference. The noble metal catalysts are used in amounts from 0.00001–0.5 parts per 100 weight parts of the ≡SiH containing polysiloxane, preferably 0.00001–0.02 parts, most preferably 0.00001–0.002 parts.

The phrase low molecular weight silicone oil (D) includes compounds containing a silicon atom such as (i) low molecular weight linear and cyclic volatile methyl siloxanes, (ii) low molecular weight linear and cyclic volatile and non-volatile alkyl and aryl siloxanes, and (iii) low molecular weight functional linear and cyclic siloxanes. Most preferred, however, are low molecular weight linear and cyclic volatile methyl siloxanes (VMS).

VMS compounds correspond to the average unit formula $(CH_3)_aSiO_{(4-a)/2}$ in which a has an average value of two to three. The compounds contain siloxane units joined by ≡Si—O—Si≡ bonds. Representative units are monofunctional "M" units $(CH_3)_3SiO_{1/2}$ and difunctional "D" units $(CH_3)_2SiO_{2/2}$.

The presence of trifunctional "T" units $CH_3SiO_{3/2}$ results in the formation of branched linear or cyclic volatile methyl siloxanes. The presence of tetrafunctional "Q" units $SiO_{4/2}$ results in the formation of branched linear or cyclic volatile methyl siloxanes.

Linear VMS have the formula $(CH_3)_3SiO\{(CH_3)_2SiO\}_ySi(CH_3)_3$. The value of y is 0–5. Cyclic VMS have the formula $\{(CH_3)_2SiO\}_z$. The value of z is 3–9. Preferably, these volatile methyl siloxane have boiling points less than about 250° C. and viscosities of about 0.65 to about 5.0 centistokes ($mm^2/s$).

Representative linear volatile methyl siloxanes are hexamethyldisiloxane (MM) with a boiling point of 100° C., viscosity of 0.65 $mm^2/s$, and formula $Me_3SiOSiMe_3$; octamethyltrisiloxane (MDM) with a boiling point of 152° C., viscosity of 1.04 $mm^2/s$, and formula $Me_3SiOMe_2SiOSiMe_3$; decamethyltetrasiloxane ($MD_2M$) with a boiling point of 194° C., viscosity of 1.53 $mm^2/s$, and formula $Me_3SiO(Me_2SiO)_2SiMe_3$; dodecamethylpentasiloxane ($MD_3M$) with a boiling point of 229° C., viscosity of 2.06 $mm^2/s$, and formula $Me_3SiO(Me_2SiO)_3SiMe_3$; tetradecamethylhexasiloxane ($MD_4M$) with a boiling point of 245° C., viscosity of 2.63 $mm^2/s$, and formula $Me_3SiO(Me_2SiO)_4SiMe_3$; and hexadecamethylheptasiloxane ($MD_5M$) with a boiling point of 270° C., viscosity of 3.24 $mm^2/s$, and formula $Me_3SiO(Me_2SiO)_5SiMe_3$.

Representative cyclic volatile methyl siloxanes are hexamethylcyclotrisiloxane ($D_3$) a solid with a boiling point of 134° C. and formula $\{(Me_2)SiO\}_3$; octamethylcyclotetrasiloxane ($D_4$) with a boiling point of 176° C., viscosity of 2.3 $mm^2/s$, and formula $\{(Me_2)SiO\}_4$; decamethylcyclopentasiloxane ($D_5$) with a boiling point of 210° C., viscosity of 3.87 $mm^2/s$, and formula $\{(Me_2)SiO\}_5$; and dodecamethylcyclohexasiloxane ($D_6$) with a boiling point of 245° C., viscosity of 6.62 $mm^2/s$, and formula $\{(Me_2)SiO\}_6$.

Representative branched volatile methyl siloxanes are heptamethyl-3-{(trimethylsilyl)oxy}trisiloxane ($M_3T$) with a boiling point of 192° C., viscosity of 1.57 $mm^2/s$, and formula $C_{10}H_{30}O_3Si_4$; hexamethyl-3,3, bis {(trimethylsilyl) oxy} trisiloxane ($M_4Q$) with a boiling point of 222° C., viscosity of 2.86 $mm^2/s$, and formula $C_{12}H_{36}O_4Si_5$;and pentamethyl {(trimethylsilyl)oxy} cyclotrisiloxane ($MD_3$) with the formula $C_8H_{24}O_4Si_4$.

Our process also includes using low molecular weight linear and cyclic volatile and non-volatile alkyl and aryl siloxanes represented respectively by formulas $R_3SiO(R_2SiO)_ySiR_3$ and $(R_2SiO)_z$. R can be alkyl groups with 2–20 carbon atoms or aryl groups such as phenyl. The value of y is 0–80, preferably 5–20. The value of z is 3–9, preferably 4–6. These polysiloxanes have viscosities generally in the range of about 1–100 centistokes ($mm^2/s$). Polysiloxanes can also be used where y has a value sufficient to provide polymers with a viscosity in the range of about 100–1,000 centistokes ($mm^2/sec$). Typically, y can be about 80–375. Illustrative of such polysiloxanes are polydimethylsiloxane, polydiethylsiloxane, polymethylethylsiloxane, polymethylphenylsiloxane, and polydiphenylsiloxane.

Low molecular weight functional polysiloxanes can also be employed, and are represented by the formula $R_3SiO(RQSiO)_ySiR_3$ where Q is a functional group. Examples of such functional polysiloxanes containing functional groups represented by Q are acrylamide functional siloxane fluids, acrylate functional siloxane fluids, amide functional siloxane fluids, amino functional siloxane fluids, carbinol functional siloxane fluids, carboxy functional siloxane fluids, chloroalkyl functional siloxane fluids, epoxy functional siloxane fluids, glycol functional siloxane fluids, ketal functional siloxane fluids, mercapto functional siloxane fluids, methyl ester functional siloxane fluids, perfluoro functional siloxane fluids, and silanol functional siloxanes.

Our invention is not limited to swelling silicone elastomers with only low molecular weight polysiloxanes. Other types of solvents can swell the silicone elastomer. Thus, a single solvent or a mixture of solvents may be used.

By solvent we mean (i) organic compounds, (ii) compounds containing a silicon atom as enumerated above, (iii) mixtures of organic compounds, (iv) mixtures of compounds containing a silicon atom, or (v) mixtures of organic compounds and compounds containing a silicon atom; used on an industrial scale to dissolve, suspend, or change the physical properties of other materials.

In general, the organic compounds are aromatic hydrocarbons, aliphatic hydrocarbons, alcohols, aldehydes, ketones, amines, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, and mineral spirits; alkyl halides such as chloroform, carbon tetrachloride, perchloroethylene, ethyl chloride, and chlorobenzene; aromatic hydrocarbons such as benzene, toluene, ethylbenzene, and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether, and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil, and whale oil.

"Other" miscellaneous organic solvents can also be used, such as acetonitrile, nitromethane, dimethylformamide, propylene oxide, trioctyl phosphate, butyrolactone, furfural, pine oil, turpentine, and m-creosol.

We further intend to encompass by the term solvent, volatile flavoring agents such as oil of wintergreen; peppermint oil; spearmint oil; menthol; vanilla; cinnamon oil; clove oil; bay oil; anise oil; eucalyptus oil; thyme oil; cedar leaf oil; oil of nutmeg; oil of sage; cassia oil; cocoa; licorice; high fructose corn syrup; citrus oils such as lemon, orange, lime, and grapefruit; fruit essences such as apple, pear, peach, grape, strawberry, raspberry, cherry, plum, pineapple, and apricot; and other useful flavoring agents including aldehydes and esters such as cinnamyl acetate, cinnamaldehyde, eugenyl formate, p-methylanisole, acetaldehyde, benzaldehyde, anisic aldehyde, citral, neral, decanal, vanillin, tolyl aldehyde, 2,6-dimethyloctanal, and 2-ethyl butyraldehyde.

In addition, we intend the term solvent to include volatile fragrances such as natural products and perfume oils. Some representative natural products and perfume oils are ambergris, benzoin, civet, clove, leaf oil, jasmine, mate', mimosa, musk, myrrh, orris, sandalwood oil, and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Carrying out of the process is simply a matter of combining the ≡SiH containing polysiloxane(s), the alpha-olefin, the alpha, omega-diene, the low molecular weight silicone oil or other solvent, and the catalyst; and mixing these ingredients at room temperature until a gel is formed. Higher temperatures to speed up the process can be used, if desired.

Additional amounts of the low molecular weight silicone oil or solvent are then added to the gel, and the resulting mixture is subjected to shear force to form the paste. Any type of mixing and shearing equipment may be used to perform these steps such as a batch mixer, planetary mixer, single or multiple screw extruder, dynamic or static mixer, colloid mill, homogenizer, sonolator, or a combination thereof.

Typically, we carry out the process using approximately a 1:1 molar ratio of ≡Si—H containing polysiloxane to vinyl groups from the alpha-olefin and the alpha, omega-diene. It is expected that useful materials may also be prepared by carrying out the process with an excess of the ≡Si—H containing polysiloxane or the vinyl containing compounds, but this would be considered a less efficient use of the materials. The remainder of the composition comprises the low molecular weight silicone oil or other solvent in amounts generally within the range of about 65–98 percent by weight of the composition, preferably about 80–98 percent by weight.

Most preferably, however, the low molecular weight silicone oil is thickened by the silicone elastomers in a two-step process. In the first step, the ≡SiH containing polysiloxane is grafted with long alkyl groups by contacting it with the alpha-olefin in the presence of the platinum catalyst. In the second step, the ≡SiH containing polysiloxane grafted with long alkyl groups from the alpha-olefin is crosslinked by contact with the alpha, omega-diene, in the presence of the low molecular weight silicone oil and the platinum catalyst. An elastomer with a more hydrocarbon character is thereby produced, compared to elastomers made by using only an alpha, omega-diene. A representation of this two-step process is shown below:

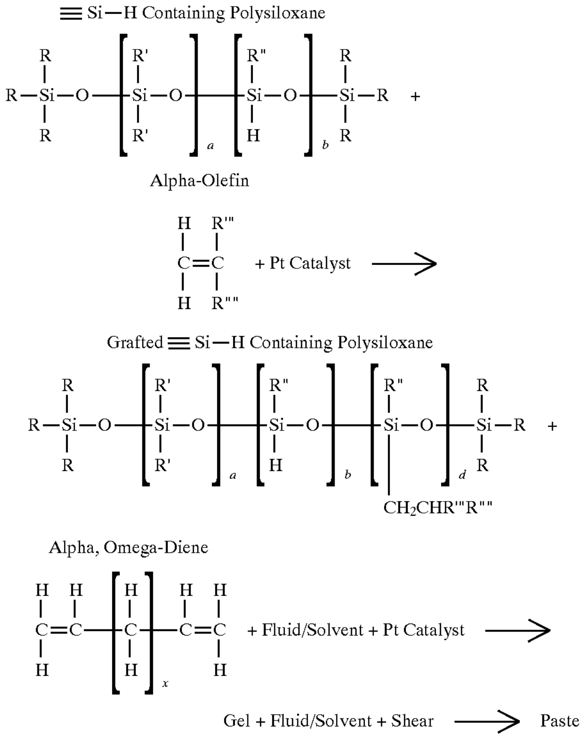

Alternatively, thickening with silicone elastomers can be carried out in one-step by gelation of a mixture including the ≡SiH containing polysiloxane, the alpha-olefin, the alpha, omega-diene, the low molecular weight silicone oil, and the platinum catalyst. Silicone elastomers made in one-step or two-steps are equally capable of being swollen with the low molecular weight silicone oil under shear force, and both processes provide uniform silicone pastes. While these silicone pastes have excellent spreadability upon rubbing, and possess unique rheological properties in being thixotropic and shear thinning, as noted above, they possess the added benefit of being more compatible with hydrophobic materials such as mineral oil.

The following examples are set forth to illustrate our invention in more detail.

EXAMPLE 1

100 grams of an organopolysiloxane with the average structure $Me_3SiO(Me_2SiO)_{60}(MeHSiO)_8SiMe_3$ where Me represents methyl, and 17.55 grams of an alpha-olefin with the average structure $CH_2{=}CH(CH_2)_{24}CH_3$ were mixed in a flask. To this solution was added 20 $\mu$l of Karstedt's catalyst described above, containing two weight percent platinum in a two centistoke ($mm^2/s$) polydimethylsiloxane fluid. This solution was stirred for about 3 hours. The resulting product (14 grams) and alpha, omega-diene 1,5-hexadiene (0.542 grams) were mixed with 66 grams of decamethylcyclopentasiloxane ($D_5$) in a reaction vessel. 20 $\mu$l of Karstedt's catalyst was again added while the solution was stirred. Gelation occurred within one hour. The gel was left in the reaction flask overnight, and then 60 parts by weight of the gel were swollen with 46 parts by weight of decamethylcyclopentasiloxane under a shear force. A uniform paste was obtained having a viscosity of $1.08\times10^6$ centipoise (mPa·s) at a shear rate of 0.025 reciprocal seconds ($s^{-1}$). The paste was mixed with mineral oil, and found to be compatible with mineral oil in any weight ratio. This example illustrates the two-step method.

EXAMPLE 2

25 grams of an organopolysiloxane with the average structure $Me_3SiO(Me_2SiO)_{16}(MeHSiO)_{39}SiMe_3$ where Me is methyl, and 49 grams of alpha-olef in $CH_2{=}CH(CH_2)_{15}CH_3$ were mixed in a flask. To this solution was added 20 $\mu$l of Karstedt's catalyst used in Example 1, and the solution was stirred for one hour. This product (3 grams), 5 grams of an organopolysiloxane with the average structure $Me_3SiO(Me_2SiO)_{93}(MeHSiO)_6SiMe_3$, and 1,5-hexadiene (0.285 grams), were mixed with 37 grams of decamethylcyclopentasiloxane in a reaction vessel. 20 $\mu$l of Karstedt's catalyst was again added while the solution was stirred. Gelation took place within a few hours. The gel was placed in an 80° C. oven for three hours, and then 43 parts by weight of the gel were swollen with 34 parts by weight of decamethylcyclopentasiloxane under a shear force. A uniform paste was obtained with a viscosity of $5.77\times10^5$ centipoise (mPa·s) at a shear rate of 0.025 reciprocal seconds ($s^{-1}$). The paste was mixed with mineral oil, and found to be compatible with mineral oil in any weight ratio. This example also illustrates the two-step method.

EXAMPLE 3

In a reaction vessel, 15 grams of an organopolysiloxane with the average structure $Me_3SiO(Me_2SiO)_{60}(MeHSiO)_8SiMe_3$ where Me is methyl, 1.24 grams of alpha-olefin $CH_2{=}CH(CH_2)_{15}CH_3$, 0.73 grams of alpha, omega-diene 1,5-hexadiene, and 68 grams of decamethylcyclopentasiloxane were mixed together. To this solution was added 20 $\mu$l of Karstedt's catalyst used in Examples 1 and 2. The solution was stirred until it gelled. The gel was placed in an 80° C. oven for four hours, and then 50 parts by weight of the gel were swollen with 50 parts by weight of decamethylcyclopentasiloxane under a shear force. A uniform paste was obtained with a viscosity of $1.9\times10^6$ centipoise (mPa·s) at a shear rate of 0.025 reciprocal seconds ($s^{-1}$). The paste was mixed with mineral oil, and found to be compatible with mineral oil in any weight ratio. This example illustrates the one-step method.

EXAMPLE 4 —Comparison Example

A gel was made from 12 grams of an organopolysiloxane with the average structure $Me_3SiO(Me_2SiO)_{93}(MeHSiO)_6SiMe_3$ where Me is methyl, 0.412 grams of alpha, omega-diene 1,5-hexadiene, 80.7 grams of decamethylcyclopentasiloxane, and 20 $\mu$l of Karstedt's catalyst used in Examples 1–3. Sixty grams of this gel were swollen with 34 grams of decamethylcyclopentasiloxane under a shear force. A paste was obtained and mixed with mineral oil. The paste and mineral oil had poor compatibility. This was evidenced by the development of haziness, and the eventual phase separation which occurred.

Silicone pastes prepared according to Examples 1–3 are compatible with emollient oils other than mineral oil, such as peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, octyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, N.J.; hydrocarbons such as petrolatum and squalane; and mixtures of branched chain hydrocarbons sold under the tradename ISOPAR by the Exxon Chemical Company, Houston, Tex.

The silicone elastomer, silicone gel, silicone paste, and silicone powder compositions of our invention have particular value in the personal care arena. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and will improve the properties of skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, and shaving lathers. They can be used in hair shampoos, hair conditioners, hair sprays, mousses, permanents, depilatories, and cuticle coats, to enhance gloss and drying time, and provide conditioning benefits.

In cosmetics, they will function as leveling and spreading agents for pigments in make-ups, color cosmetics, foundations, blushes, lipsticks, lip balms, eyeliners, mascaras, oil removers, color cosmetic removers, and powders. They are useful as delivery systems for oil and water soluble substances such as vitamins. When incorporated into sticks, gels, lotions, aerosols, and roll-ons, the compositions impart a dry, silky-smooth, payout.

In addition, the compositions exhibit a variety of advantageous and beneficial properties such as clarity, shelf stability, and ease of preparation. Hence, they have wide application, but especially in antiperspirants, deodorants, in perfumes as a carrier, and for conditioning hair.

Our silicone elastomers, gels, pastes, and powders, have uses beyond the personal care arena, including their use as a filler or insulation material for electrical cable, a soil or water barrier for in-ground stabilization, or as a replacement for epoxy materials used in coil-on-plug designs in the electronics industry.

They are also useful as carrier for crosslinked silicone rubber particles. In that application, (i) they allow ease of incorporation of the particles into such silicone or organic phases as sealants, paints, coatings, greases, adhesives, antifoams, and potting compounds; and (ii) they provide for modifying rheological, physical, or energy absorbing properties of such phases in either their neat or finished condition.

In addition, our silicone elastomers, gels, pastes, and powders, are capable of functioning as carriers for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid.

Other variations may be made in compounds, compositions, and methods described herein without departing from the essential features of our invention. The forms of our invention are exemplary and not limitations on its scope as defined in the claims.

What is claimed is:

1. A method of thickening solvents comprising reacting (A) a first ≡Si—H containing polysiloxane of the formula $R_3SiO(R'_2SiO)_a(R''HSiO)_bSiR_3$ and optionally a second ≡Si—H containing polysiloxane of the formula $HR_2SiO(R'_2SiO)_cSiR_2H$ or the formula $HR_2SiO(R'_2SiO)_a(R''HSiO)_bSiR_2H$ where R, R', and R" are alkyl groups of 1–6 carbon atoms; a is 0–250;b is 1–250;and c is 0–250;(B) an alpha-olefin of the formula $CH_2{=}CR'''R''''$ where R''' is hydrogen or an alkyl group containing 1–40 carbon atoms, and R'''' is an alkyl group containing 1–40 carbon atoms; and (C) an alpha, omega-diene of the formula $CH_2{=}CH(CH_2)_xCH{=}CH_2$ where x is 1–20;conducting the reaction in the presence of a platinum catalyst and (D) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and continuing the reaction until a gel is formed.

2. A method according to claim 1 including the further steps of adding additional solvent to the gel, and subjecting the solvent and the gel to shear force until a paste is formed.

3. A method according to claim 1 including the further step of using mechanical force to crumble the gel until a powder is obtained.

4. A gel prepared according to the method in claim 1.

5. A paste prepared according to the method in claim 2.

6. A powder prepared according to the method in claim 3.

7. A product containing the gel of claim 4 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, cosmetic removers, delivery systems for oil and water soluble substances, and pressed powders; wherein the products may be in the form of sticks, gels, lotions, aerosols, or roll-ons.

8. A product containing the gel of claim 4 and a material selected from the group consisting of crosslinked silicone rubber particles, pharmaceuticals, biocides, herbicides, pesticides, water, and water-soluble substances.

9. A method of treating hair or skin comprising applying to the hair or skin a product of claim 7.

10. A method of modifying rheological, physical, or energy absorbing properties, of silicone or organic phases selected from the group consisting of sealants, paints, coatings, greases, adhesives, antifoams, and potting compounds, comprising incorporating therein the gel of claim 4 containing crosslinked silicone rubber particles.

11. A method of filling or insulating an electrical cable comprising incorporating therein the gel of claim 4.

12. A method of stabilizing in-ground soil or water barriers comprising incorporating into soil the gel of claim 4.

13. A method of thickening solvents comprising a first step of reacting (A) a first ≡Si—H containing polysiloxane of the formula $R_3SiO(R'_2SiO)_a(R''HSiO)_bSiR_3$ and optionally a second ≡Si—H containing polysiloxane of the formula $HR_2SiO(R'_2SiO)_cSiR_2H$ or the formula $HR_2SiO(R'_2SiO)_a(R''HSiO)_bSiR_2H$ where R, R', and R" are alkyl groups of 1–6 carbon atoms; a is 0–250;b is 1–250; and c is 0–250; with (B) an alpha-olefin of the formula $CH_2{=}CR'''R''''$ where R''' is hydrogen or an alkyl group containing 1–40 carbon atoms, and R''' is an alkyl group containing 1–40 carbon atoms; conducting the reaction in the presence of a platinum catalyst; continuing the reaction until the alpha-olefin is grafted onto the ≡Si—H containing polysiloxane; then adding (C) an alpha, omega-diene of the formula $CH_2{=}CH(CH_2)_xCH{=}CH_2$ where x is 1–20; conducting the reaction in the presence of a platinum catalyst and (D) a solvent selected from the group consisting of (i) organic compounds, (ii) compounds containing a silicon atom, (iii) mixtures of organic compounds, (iv) mixtures of compounds containing a silicon atom, and (v) mixtures of organic compounds and compounds containing a silicon atom; and continuing the reaction until a gel is formed.

14. A method according to claim 13 including the further steps of adding additional solvent to the gel, and subjecting the solvent and the gel to shear force until a paste is formed.

15. A method according to claim 13 including the further step of using mechanical force to crumble the gel until a powder is obtained.

16. A gel prepared according to the method in claim 13.

17. A paste prepared according to the method in claim 14.

18. A powder prepared according to the method in claim 15.

19. A product containing the gel of claim 16 selected from the group consisting of antiperspirants, deodorants, skin creams, skin care lotions, moisturizers, acne removers, wrinkle removers, facial cleansers, bath oils, perfumes, colognes, sachets, sunscreens, pre-shave lotions, after-shave lotions, liquid soaps, shaving soaps, shaving lathers, hair shampoos, hair conditioners, hair sprays, mousses, permanents, depilatories, cuticle coats, make-ups, color cosmetics, foundations, blushes, lipsticks, lip balms, eyeliners, mascaras, oil removers, cosmetic removers, delivery systems for oil and water soluble substances, and pressed powders; wherein the products may be in the form of sticks, gels, lotions, aerosols, or roll-ons.

20. A product containing the gel of claim 16 and a material selected from the group consisting of crosslinked silicone rubber particles, pharmaceuticals, biocides, herbicides, pesticides, water, and water-soluble substances.

21. A method of treating hair or skin comprising applying to the hair or skin a product of claim 19.

22. A method of modifying rheological, physical, or energy absorbing properties, of silicone or organic phases selected from the group consisting of sealants, paints, coatings, greases, adhesives, antifoams, and potting compounds, comprising incorporating therein the gel of claim 16 containing crosslinked silicone rubber particles.

23. A method of filling or insulating an electrical cable comprising incorporating therein the gel of claim 16.

24. A method of stabilizing in-ground soil or water barriers comprising incorporating into soil the gel of claim 16.

* * * * *